(12) United States Patent
Angeli et al.

(10) Patent No.: US 11,166,854 B2
(45) Date of Patent: Nov. 9, 2021

(54) METHOD FOR PRODUCING A PERFORATED WEB AND PRODUCT FOR A SANITARY ABSORBENT ARTICLE THEREOF

(71) Applicant: Pantex International S.p.A., Sulmona (IT)

(72) Inventors: Pietro Angeli, Sulmona (IT); Gianluigi Fornoni, Sulmona (IT); Carmine Di Benedetto, Sulmona (IT); Antonio Caira, Sulmona (IT)

(73) Assignee: PANTEX INTERNATIONAL SPA, Sulmona (IT)

( * ) Notice: Subject to any disclaimer, the term of this patent is extended or adjusted under 35 U.S.C. 154(b) by 1226 days.

(21) Appl. No.: 15/302,950

(22) PCT Filed: Apr. 8, 2015

(86) PCT No.: PCT/IB2015/052558
§ 371 (c)(1),
(2) Date: Oct. 7, 2016

(87) PCT Pub. No.: WO2015/155714
PCT Pub. Date: Oct. 15, 2015

(65) Prior Publication Data
US 2017/0035619 A1    Feb. 9, 2017

(30) Foreign Application Priority Data

Apr. 8, 2014  (IT) .......................... TO2014A000299

(51) Int. Cl.
*A61F 13/15*    (2006.01)
*A61F 13/512*   (2006.01)
(Continued)

(52) U.S. Cl.
CPC .. *A61F 13/15731* (2013.01); *A61F 13/15707* (2013.01); *A61F 13/512* (2013.01);
(Continued)

(58) Field of Classification Search
CPC .................. B29C 59/04; B29C 59/025; B29C 2793/0045; A61F 13/15731; A61F 13/512;
(Continued)

(56) References Cited

U.S. PATENT DOCUMENTS

2005/0234414 A1* 10/2005 Liu ........................ A61F 13/42
604/361
2006/0184150 A1* 8/2006 Noel ..................... A61F 13/532
604/383
(Continued)

FOREIGN PATENT DOCUMENTS

EP      2353809      8/2011
WO      96/39109     12/1996
(Continued)

OTHER PUBLICATIONS

European Patent Office, International Search Report, dated Aug. 6, 2015.
(Continued)

*Primary Examiner* — Jeffrey M Wollschlager
(74) *Attorney, Agent, or Firm* — Leason Ellis LLP (57) ABSTRACT

A method for producing a low density perforated web material having a thickness of at least 0.20 mm, comprising the steps of:
  providing a layer of low density material having a maximum overall weight per square meter of 75 g/m² or less; and
  processing the low density material between two rollers pressing onto each other to obtain a low density per-
(Continued)

forated web material, wherein a first roller has protrusions to perforate the low density material, and a second roller rotates at a different speed from that of the first roller and has projecting parts with contact areas arranged to perforate the material with the protrusions, the contact areas being spaced by recesses to receive the material and having larger contact face dimensions than the protrusions, the recesses leaving an impression in relief on the low density polymer material.

13 Claims, 7 Drawing Sheets

(51) Int. Cl.
*B29C 59/04* (2006.01)
*B29C 59/02* (2006.01)

(52) U.S. Cl.
CPC ............ *B29C 59/04* (2013.01); *B29C 59/025* (2013.01); *B29C 2793/0045* (2013.01)

(58) Field of Classification Search
CPC .............. A61F 13/5121; A61F 13/5122; A61F 13/5123; A61F 13/5125; A61F 13/5126; A61F 13/5127; A61F 13/5128
See application file for complete search history.

(56) References Cited

U.S. PATENT DOCUMENTS

| | | | | |
|---|---|---|---|---|
| 2012/0273997 | A1* | 11/2012 | Stone | B29C 55/18 |
| | | | | 264/280 |
| 2012/0276331 | A1* | 11/2012 | Orr | B29C 53/24 |
| | | | | 428/137 |
| 2012/0316532 | A1* | 12/2012 | McCormick | A61F 13/51104 |
| | | | | 604/372 |
| 2015/0173975 | A1* | 6/2015 | Harumoto | B32B 7/06 |
| | | | | 604/370 |

FOREIGN PATENT DOCUMENTS

| | | | |
|---|---|---|---|
| WO | WO2005011936 | * | 2/2005 |
| WO | 2013/163360 | | 10/2013 |
| WO | WO2014023090 | * | 2/2014 |

OTHER PUBLICATIONS

European Patent Office, Written Opinion of the International Searching Authority, dated Aug. 6, 2015.

* cited by examiner

METHOD FOR PRODUCING A PERFORATED WEB AND PRODUCT FOR A SANITARY ABSORBENT ARTICLE THEREOF

CROSS-REFERENCE TO RELATED APPLICATIONS

The present application is a U.S. national stage of, and claims the priority benefit of, International Patent Application Serial No. PCT/IB2015/052558, filed Apr. 8, 2015 and Italian Patent Application Serial No. TO2014A000299, filed Apr. 8, 2014, the text and drawings of which are hereby incorporated by reference in their entireties.

TECHNICAL FIELD

The present invention refers to a method for producing perforated low density web material and a product obtained by means of said method for absorbent sanitary articles, for example nappies, sanitary towels or incontinence pads.

BACKGROUND ART

A perforated low density web material is preferably used as a surface layer in contact with the skin in an absorbent sanitary article. It may be either fibrous (web) or continuous (film).

Said layer performs numerous functions and the morphological and physical characteristics are designed to obtain high performance taking account of the following requirements.

A perforated low density web material acts as an interface for the collection of body fluids deposited on the sanitary article and subsequently absorbed and retained by dedicated layers, for example cellulose fibre-based, arranged below the low density perforated material. In said regard it is important to facilitate the flow of fluid towards the absorbent layer to ensure rapid absorption by the cellulose layer.

Furthermore the absorbent sanitary article is normally subject to a pressure, like the one due to the body weight of a user in a sitting position, which compresses the absorbent layer and can generate a rewet of the body fluid towards the user's skin. Said rewet should be as limited as possible.

In addition to the cited requirements concerning the barrier function performed by the low density perforated material, the importance of comfort requirements for the user must be considered both when the absorbent sanitary article is dry and, to an even greater extent, when the absorbent sanitary article has to retain a body fluid. Comfort refers, among other things, to the following characteristics, each of which produces a specific user sensation when the absorbent sanitary article is worn.

In particular, softness is understood as a tactile sensation when brushing against the surface in contact with the skin.

The cushioning effect refers to the capacity of a layer to return to its initial thickness after being compressed.

The requirement of pliability means that it is preferable for the layer in contact with the skin to form extremely pliable folds after flexions of the absorbent sanitary article due to adhesion to the user's body and/or the normal movements of the latter when wearing the absorbent sanitary article.

Furthermore the use of low cost materials is always preferable.

Some inexpensive materials are continuous polymer web materials, i.e. not low density like film. To meet in particular the requirement of pliability, continuous web materials are used with very low thicknesses, in particular less than 0.1 mm. Nevertheless, the overall performance of single-layer continuous polymer web materials, i.e. considering all the requirements, are not satisfactory.

The use of low density webs for the layers in contact with the skin of absorbent sanitary articles is known. Low density webs, while having higher costs than films, have better performance in particular in terms of pliability.

EP-A-2353809 describes a calender for a perforated web polymer material in particular for an absorbent sanitary article for body fluids.

The calender comprises a first roller and a second roller pressing onto each other, each of which has respective series of projections surrounded by recesses. When two heads of respective projections come into contact with each other, a localised perforation is performed on the web. The perforation is further facilitated by the fact that the rollers have different peripheral speeds, hence both a pressure on a plane comprising both axes of the rollers and an action perpendicular to said plane is applied to the web material. The latter action, defined by the relative slipping between the rollers, causes a localised tearing of the web at the heads in contact with two opposite projections.

In particular, it is specified that the web material tends to penetrate into the recesses of the rollers, increasing the final thickness of the web due to accumulation of the material during the process between the rollers. By means of the increase in thickness following processing in the calender, it is possible to obtain an improved sensation of softness since the areas having an increased thickness have a temperature below that of the contour of each perforated hole.

The use of a calender with slipping rollers allows the production of a low density perforated web material at particularly low costs.

However, the teaching of EP-A-2353809 for increasing the thickness of the material processed can be further improved, in particular to increase performance with reference to the cushioning effect of the layer of the absorbent sanitary article in contact with the skin.

DISCLOSURE OF INVENTION

The object of the present invention is to identify a method for the production of a low density perforated web material able to meet, at least partly, the above needs.

The object of the present invention is achieved by selecting physical and morphological characteristics of a low density web material to be processed in a calender having slipping perforation rollers in which one roller has perforation protrusions and another roller has contact surfaces spaced by recesses inside which the processed material is accommodated when the contact surfaces are facing the protrusions. In particular, a good compromise is obtained between cushioning effect, softness and pliability by processing a material which has an overall thickness of at least 0.2 mm and an overall weight per square meter of less than 75 g/m². Said material, given the high air content due to the specific ratio between thickness and weight per square meter, tends to maintain constant or to slightly reduce its thickness after the process between the two rollers.

BRIEF DESCRIPTION OF THE DRAWINGS

The invention will now be described with reference to the accompanying drawings, which illustrate a non-limiting implementation example thereof, in which.

BEST MODE FOR CARRYING OUT THE INVENTION

Figure 1:
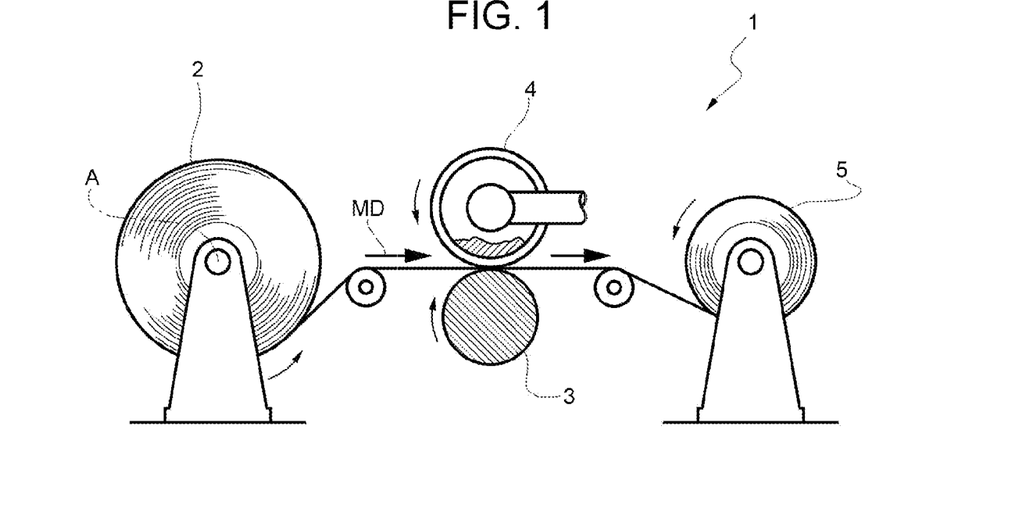
FIG. 1 is a schematic lateral view of a calender for a web material according to the present invention.

In FIG. 1 the number 1 illustrates as a whole a calender for processing web material for producing absorbent sanitary articles.

The calender 1 comprises a reel of raw material 2, for example a non-woven fabric of low density polymer web material, and a pair of opposite rollers 3, 4 in contact with each other. The rollers 3, 4 are motorised and able to slip with respect to each other while they process the non-woven fabric. After the passage between the rollers 3, 4 the processed non-woven fabric is wound on an outlet reel 5.

Figure 2:
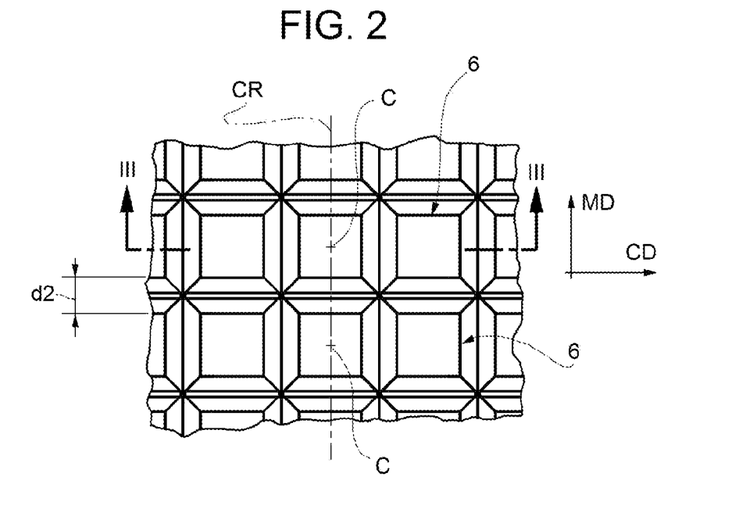
FIG. 2 is a plan view of a detail of FIG. 1.
Figure 3:
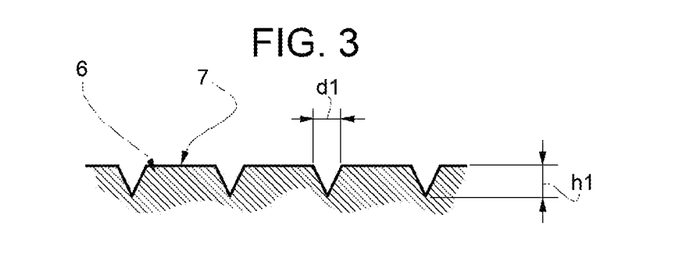
FIG. 3 is a section according to the line of FIG. 2.

In particular, the reel 3 comprises a plurality of protrusions 6 each of which has a head 7 defining a contact face, polygonal in the specific example. The protrusions 6 are preferably tapered so that the contact faces 7 are spaced from one another by a distance d1 in the cross direction (CD) parallel to a rotation axis A of the reel 2 and the rollers 3, 4. The contact faces 7 are also spaced in the machine direction (MD), i.e. in the feed direction of the non-woven fabric between the rollers 3, 4.

Figure 4:
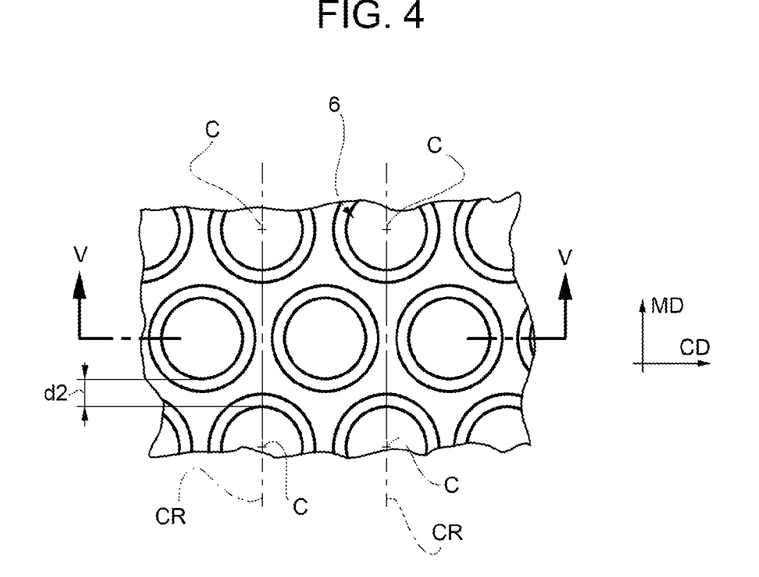
FIG. 4 is a plan view of the details of FIG. 2 according to a further embodiment of the present invention.
Figure 5:
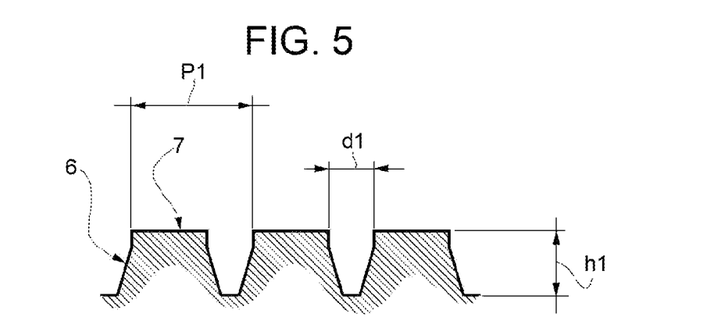
FIG. 5 is a section according to the line V-V of FIG. 4.

FIG. 4 illustrates an alternative embodiment of the protrusions 6 and the contact faces 7. The former can have sides with non-constant inclination while the latter can have a circular shape. For example, the contact faces 7 have a diameter of 0.75 mm and a pitch P1 in the cross direction (CD) of 1.2 mm and a pitch in the machine direction (MD) of 2.08 mm. The height h1 is 0.5 mm.

According to FIGS. 2 and 4, the contact faces 7 have geometric centres C aligned along reference circumferences CR which can be either parallel (as illustrated in the figures) to the direction MD or inclined with respect to the latter, preferably by maximum 10°.

The roller 4 has in turn projecting parts 8 delimited by means of recesses 9. Each projecting part 8 has a head 10 defining a contact area having a greater extension than that of the contact faces 7.

Figure 7:
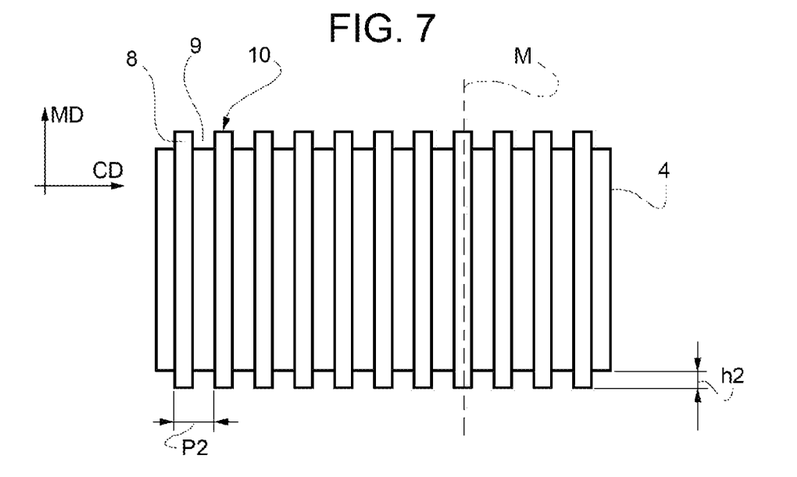
FIG. 7 is a plan view of a component of the calender of FIG. 1.
Figure 8:
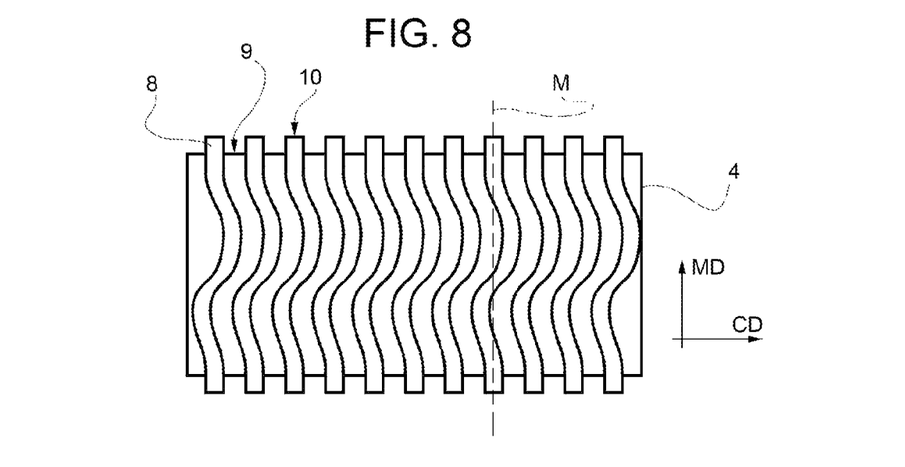
FIG. 8 is a plan view of the component of FIG. 7 according to a further embodiment of the present invention.

Preferably, the contact areas 10 are elongated, for example rectangular, ellipsoidal or similar, and have a form factor between length and width equal to or higher than 4 to facilitate diffusion of the biological liquid on the surface of the low density web material. The width of the contact areas 10 is at least 1 mm. Preferably, the contact areas 10 are closed in a circumferential direction as illustrated in FIGS. 7 and 8. A median axis M of the contact areas can be parallel to the machine direction (MD) (as illustrated in FIGS. 7 and 8) or inclined with respect to the latter. FIG. 8 illustrates a contact area 10 having an undulating profile, preferably periodic, even more preferably sinusoidal. In said case the median axis M is located in the median position with respect to which the profile diverges towards the right or towards the left. The maximum height of the projecting parts 8 which coincides with the maximum depth of the recesses 9 is greater than 1 mm, preferably approximately 1.5 mm. A pitch P2 in the cross direction (CD) of the projecting parts 8 can be 4 mm.

Figure 6:
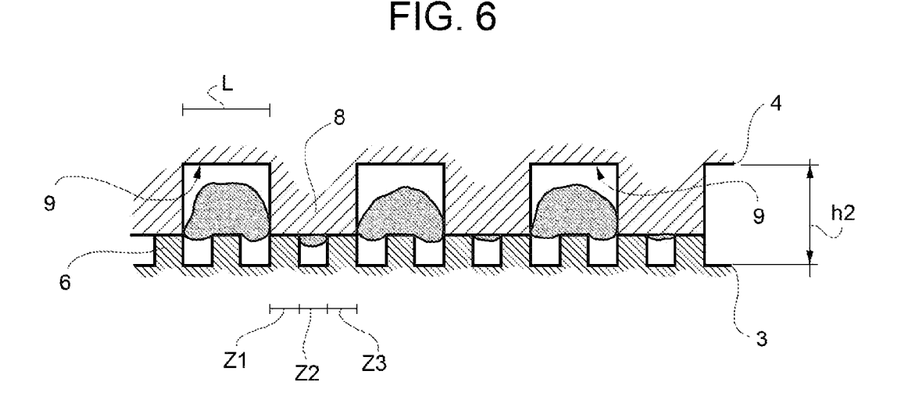
FIG. 6 is a schematic view not to scale of a detail of FIG. 1 according to the direction indicated by the arrow MD.

FIG. 6 illustrates qualitatively the low density web material during the process between the rollers 3 and 4. In particular it has been verified that when the low density web material has a weight per square meter of less than 75 $g/m^2$ and a height when fed out of the rollers 3, 4 equal to or greater than 0.2 mm, the fibres or the cells of low density web material are compressed between the contact faces 7 and the contact areas 10 while the thickness of the material remains substantially constant or is reduced, in any case less than that occurring in the zone interposed between the contact faces 7 and the contact areas 10, at the recesses 9. This occurs because the low density web materials, having a minimum thickness of 0.2 mm and a weight per square meter equal to or less than 75 $g/m^2$, have a high quantity of air inside due to the presence of fibres and/or closed cells (see example IV). Said air is completely expelled in the zones Z1 compressed between the contact faces 7 and the contact areas 10; a minimum part of the air is retained in the zone Z2 between two protrusions 6 both in contact with the same contact face 10 and it remains substantially the same or decreases less than the zone Z2 at the recesses 9. Therefore, if a single-layer low density web material is processed having initial thickness of 0.3 mm, said thickness is maintained or is slightly lower than the initial value.

FIG. 6 illustrates a case in which the low density web material has an overall feed-in thickness less than the depth h2. According to an alternative embodiment of the present invention, the depth h2 can influence the final thickness of the low density web material. In particular, the recesses 9 tend to leave an impression on the low density web material and it is possible to process low density web materials which have an overall feed-in thickness greater than the depth h2. In this case the low density web material undergoes a sort of hot moulding and the final thickness of the low density web material is approximately equal to h2 or slightly greater. In this way it is possible to calibrate the final thickness of the low density web material, both multilayer and monolayer. The width in the cross direction (CD) of the recesses 9 is at least 3 times the pitch P1 in the cross direction (CD) of the protrusions 6 (FIG. 6 not to scale). Preferably the width of the recesses 9 is at least 5 times the pitch P1 so as to have large zones of the finished product with a substantially undeformed thickness and defining a cushioning effect. Following said form factor, in combination with the minimum thickness of 0.2 mm, it was verified that a body fluid deposited on the low density web material tends to diffuse better on a larger surface and, therefore, to reach a greater number of holes. Furthermore, the portion of the low density material accommodated in the recesses 9 improves performance in terms of the cushioning effect and the pliability.

Figure 9:
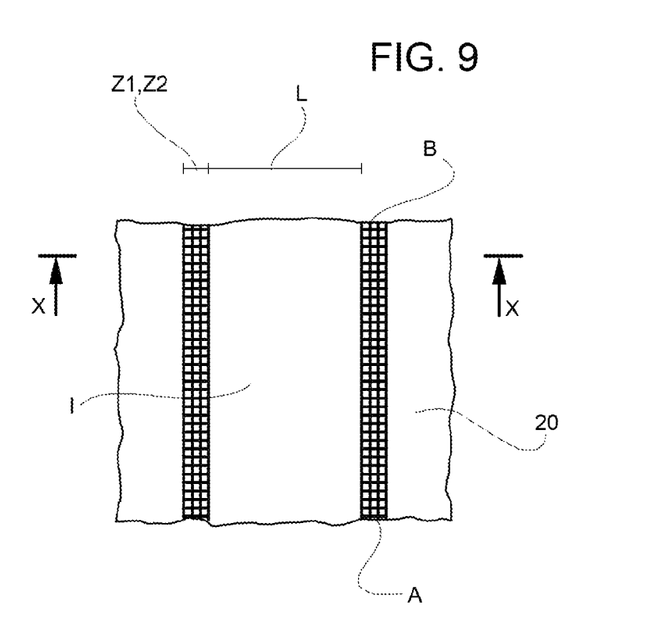
FIG. 9 is a plan view of a product obtained by means of the calender of FIG. 1.
Figure 10:
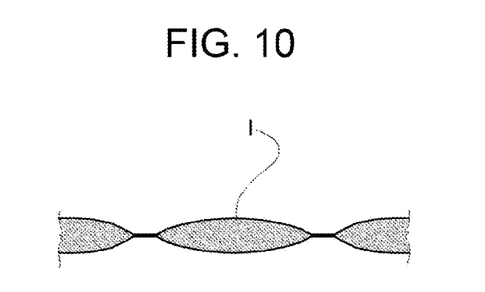
FIG. 10 is a section according to the line X-X of FIG. 9.

FIG. 9 shows a plan view of a low density web material 20 obtained by means of the method according to the present invention. As illustrated, the width of the zones Z1, Z2 which coincides with the width of the contact area 10 is approximately 5 times the width L of an impression I left in relief by the recess 9 on the web 20, but other ratios are possible.

Figure 11:
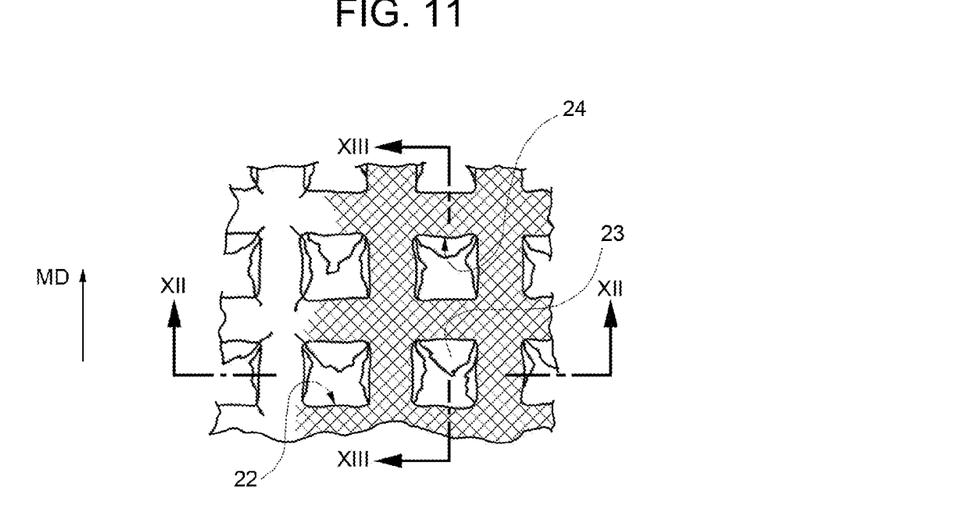
FIG. 11 is an enlarged plan view of the detail A of FIG. 9.
Figure 12:
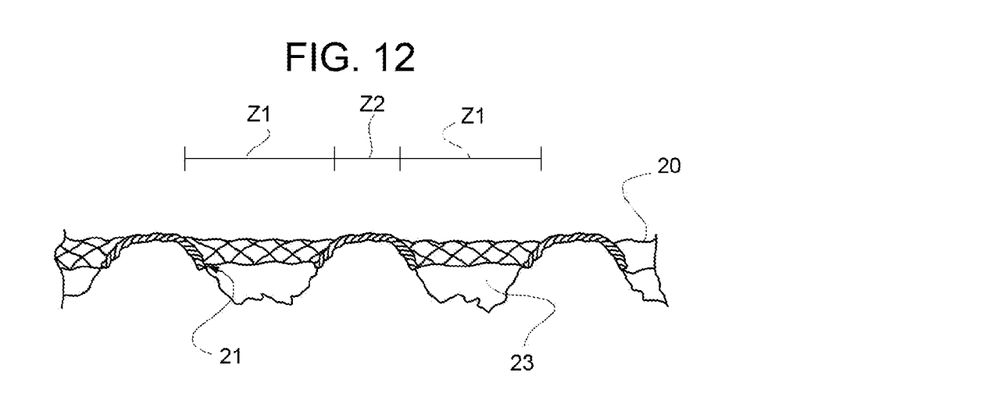
FIG. 12 is a section according to the line XII-XII of FIG. 11.
Figure 13:
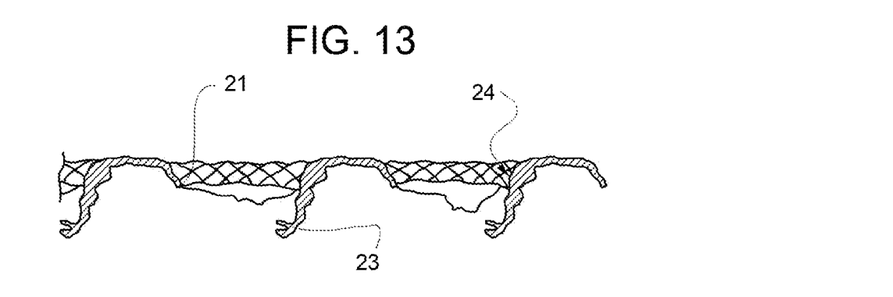
FIG. 13 is a section according to the line XIII-XIII of FIG. 11.

FIGS. 11 to 13 shows some details of the holes made in the zones Z1. As can be noted, the zones Z1 define a through perforation 21 produced since the contact face 7 locally presses the low density web material against the contact area 10 and, simultaneously, the slipping between the rollers 3, 4 applies an action that tears the material and opens the through perforation 21.

Preferably, the rollers 3, 4 are heated to temperatures between 70° and 170° degrees to soften the low density web material during the process and facilitate localised and peripheral sealing on the edge 22 of the perforation 21. The higher temperature with respect to the ambient temperature furthermore facilitates adhesion of the fibres in the zones Z2 in particular when the latter are made of a polymer material. Due to the relative slipping between the rollers 3, 4 the perforation 21 has a characteristic border 23 larger than the others and arranged on a portion 24 in the machine direction (MD) of the edge 22. Slipping due to a speed difference of approximately 30% between the rollers 3, 4 allows good quality perforations 21 to be obtained.

Figure 14:
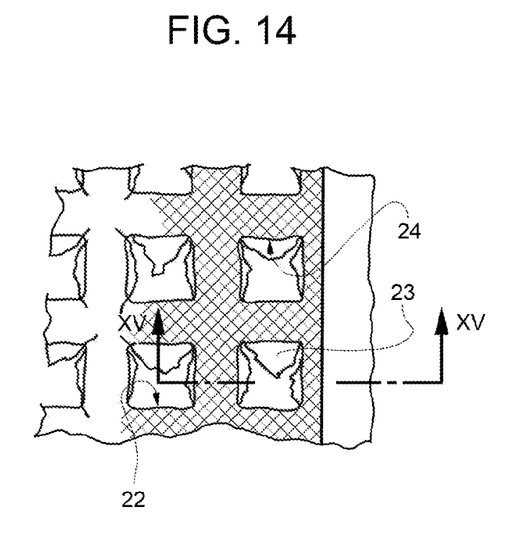
FIG. 14 is a plan view of the detail B of FIG. 9.
Figure 15:
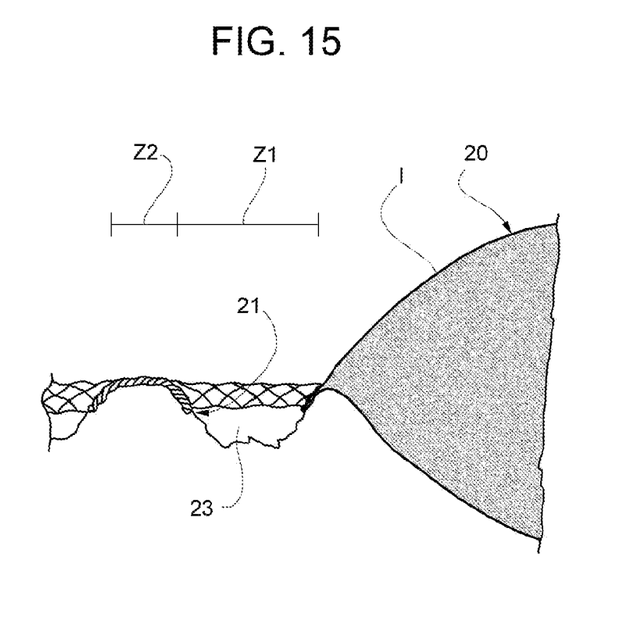
FIG. 15 is a section according to the line XV-XV of FIG. 14.

FIGS. 14, 15 illustrate details of the low density web material 20 as shaped following the process between the rollers 3, 4 in a transition zone between a contact area 10 and the adjacent recess 9. As can be noted, the zones Z1, Z2 have maximum compression but the fibres or the cells of the low density web material 20 maintain most of their initial thickness when they enter the recess 9. In particular, when a contact face 7 is on the opposite side of a recess 9 with respect to the low density web material, the latter tends to slide without any tearing, therefore no perforation is performed. The perforation is performed only by means of the combined action of the slipping between the rollers 3, 4 with the pressure exerted between the contact faces 7 and the contact areas 10.

The low density web material before the process between the rollers 3, 4 can be a monolayer or several different layers of low density web material can be combined. In both cases it is possible to establish a value of the feed-in thickness of the web material.

When low density multilayer web materials are processed, it is possible to calibrate the overall performance with reference to the strike through time measured according to the standard WSP 70.3 and the rewet measured according to the standard 80.10 combining hydrophilic and hydrophobic layers in different ways. According to the present invention, the use of a hydrophobic outer layer is preferred, which will then be in contact with the skin, in order to increase the dry sensation of the user even after the body fluid has been released.

Figure 16:
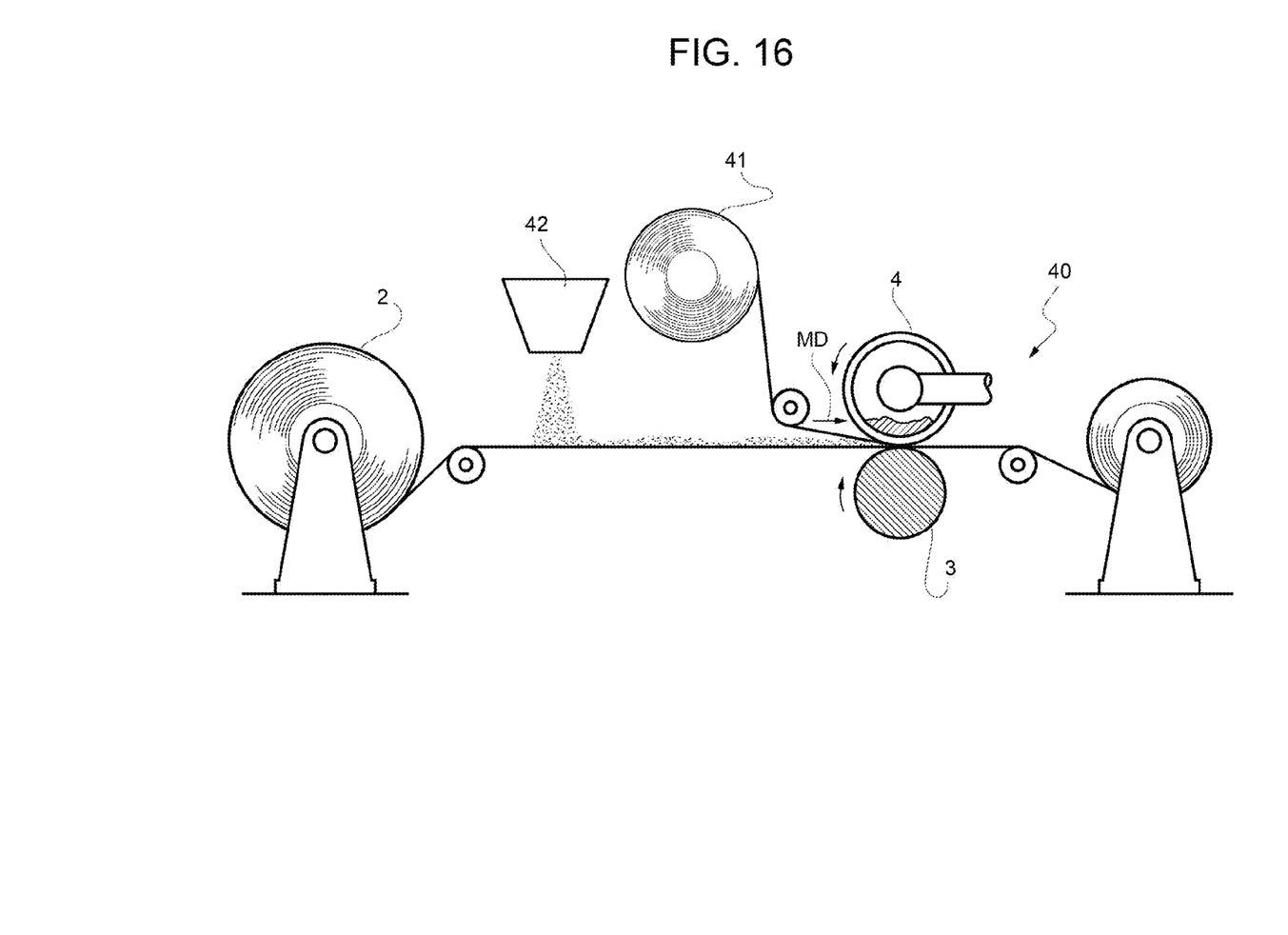
FIG. 16 is a schematic lateral view of a calender for a web material according to a further embodiment of the present invention.

Alternatively or in combination with the preceding paragraphs, it is possible to process between the rollers 3, 4 a sandwich of low density web materials and free or loose fibres deposited on one of the low density web materials before the process between the rollers 3, 4. An example of a calender 40 for producing said low density web material is illustrated in FIG. 16 where the same reference numbers as those used in FIG. 1 refer to elements functionally identical to those described in the preceding paragraphs. The machine 40 comprises in addition to the calender 1 a reel 41 for a second low density web material, for example a non-woven fabric of polymer material, and a distributor 42 of free or loose fibres. The fibres can be of any type, for example crimped, i.e. not rectilinear, both solid and tubular, i.e. having a longitudinal through cavity.

The advantages of the method according to the present invention are the following.

By processing a material that can be obtained by means of the combination of a final thickness of 0.2 mm and an overall weight per square meter of less than 75 $g/m^2$, it is possible to obtain a good compromise between cushioning effect, softness and pliability. The pliability is in particular facilitated by means of the zones Z1, Z2. In fact, the material as identified above contains inside it a large quantity of air due to the presence of closed inner fibres and/or cells.

Furthermore, it is possible to process materials with weight per square meter lower than 50 $g/m^2$, which have a particularly low cost, while nevertheless obtaining high performance. It is also possible to obtain high performance, in particular in terms of the cushioning effect, with final thicknesses equal to or greater than 0.4 mm.

Extension of the section L (FIG. 9) with respect to the pitch P1 (FIG. 5) in cross direction (CD) is at least 3 times, more preferably 5 times. Preferably the extension of the compressed or perforated sections Z1, Z2 is between 1 and 4 times the diameter or the maximum theoretical dimension of the hole, in this specific case the theoretical dimension of the hole, i.e. the diameter of the contact face 7, is 0.76 mm and the section Z1, Z2 is 1 mm wide 0.8 mm can be considered a minimum dimension of the section Z1, Z2. The ratio in cross direction (CD) between Z1, Z2 and width L is at least 1 or higher, preferably up to 5, i.e. the width L is at least equal to or higher than the sections Z1, Z2. In this way performance in terms of the cushioning effect and pliability is improved. Furthermore, softness is obtained as a consequence of the cushioning effect. More generally, the ratio between the non-perforated area, corresponding to the area of the recesses 9, and the perforated area, corresponding to the area of the contact areas 10, is 1, preferably 1.5 or higher, up to 4, maximum 5, i.e. the non-perforated area is equal to or greater than the perforated area. Said quantity can also be measured as mean area per $cm^2$ occupied by the contact areas 10. The more said area is reduced, the greater the cushioning effect. The reduction of the perforated area per unit of surface is advantageously compensated by the form factors of the recesses 9 which are elongated to leave elongated impressions I on the web product and form distribution channels of the biological fluid towards the perforations 21.

Via the coupling of hydrophobic or hydrophilic layers, when multilayers are processed, it is possible to calibrate not only the performance indicated above but also the strike through time and the rewet. Furthermore, also the fact that at least the outer layer in contact with the skin is hydrophobic helps to diffuse the biological liquid and this is particularly useful when the mean number of holes per $cm^2$ tends to decrease and in the presence of the channels.

When the protrusions 6 and/or the projecting parts 8 are not aligned or have median planes not aligned or follow paths not aligned with circumferences parallel to the machine direction (MD), wear on the rollers is reduced since the contact points between the contact faces 7 and the contact areas 10 vary in the cross direction (CD).

Some examples of low density web materials processed according to the method of the present invention are illustrated below.

In each case the height h1 of the protrusions 6 is 0.5 mm and the height h2 of the recesses 9 is 1.5 mm. The ratio between the overall surface of the recesses 9 and the overall surface of the contact areas 10 is 3 with a roller 4 analogous to that of FIG. 7. The number of perforations 21 per cm$^2$ in the areas Z1, Z2 is approximately 80. The web materials cited preferably comprise fibres of a polyolefin material.

EXAMPLE I

Monolayers

Thermally bonded bicomponent monolayer web having a weight per square meter of 25 g/m$^2$. The feed into and out of the rollers 3, 4 was maintained constant and equal to 0.25 mm.

It is further possible to process air-bonded monolayer webs having a weight per square meter of 25 g/m$^2$ to 75 g/m$^2$, preferably 35 to 65 g/m$^2$.

EXAMPLE II

A pre-bonded supporting layer is used, on which carded and therefore free fibres are deposited. When the fibres enter the calender they completely fill the recesses 9 of the cylinder 4 and hence acquire a thickness at least equal to the depth h2 or h1, thus generating projections. Said projections are very soft since the fibres are free. Said projections are in contact with the skin. The heat of the rollers 3, 4 is used to bond the fibres. To facilitate cohesion of the fibres, it is possible to add low melt fibres in a percentage between 20 and 30% of the total weight of the fibres. These fibres are more sensitive to temperature and therefore have a sealing function.

For example a low density web material was produced with the following structure:
Upper layer composed of 10 g/m$^2$ of fibres (both hydrophilic and hydrophobic fibres were used);
Thermally bonded lower layer (supporting layer) having a weight per square meter of 25 g/m$^2$ (as in example I). A total weight of 35 g/m$^2$ and a height of 0.5 mm are obtained.

EXAMPLE III

To perfectly retain the free fibres it is possible to process the following structure between the rollers 3, 4:
Upper layer: bicomponent spunbonded with low weight per square meter 10 g/m$^2$ (hydrophilic or hydrophobic);
Inner layer: free fibres (like EXAMPLE II) 15 g/m$^2$ (hydrophilic or hydrophobic);
Upper layer: bicomponent spunbonded with low weight per square meter 10 g/m$^2$ (hydrophilic or hydrophobic).

An overall weight per square meter of 35 g/m$^2$ and final thickness of 0.53 mm are obtained. A comparative example was performed in which the roller 4 was replaced with a smooth roller, all the other machine/process characteristics remaining the same. The thickness obtained in this case, with the same processed material, was 0.387 mm. In a further comparative example, with reference to the processed material, the inner layer was replaced with free fibres having weight per square meter of 10 g/m$^2$ (like EXAMPLE II). The thickness obtained following the process with the rollers 3, 4 of the invention is 0.385 mm; the thickness obtained after replacement of the roller 4 with a smooth roller is 0.36 mm.

EXAMPLE IV

A multilayer material is formed consisting of a first layer made of non-woven fabric coupled with a second layer of closed cell foamed polyethylene.

In the context of the present invention, by closed cell foamed material we mean a material consisting of "closed microcells", which make it impermeable to water, resilient, with good resistance to compression. Closed cell foamed material differs from open cell foamed material due to the fact that the cells are spaced and each one is completely surrounded by solid material. Vice versa in an open cell material there is a passage of fluid between one cell and the other, which makes the open cell material not fluid-tight. It should be noted that a closed cell material is hydrophobic and waterproof.

The first layer is a thermally bonded non-woven fabric with weight of 13 g per square metre with the characteristics given in table 1:

TABLE 1

| Characteristics | Test method | Unit of measurement | Batch mean |
|---|---|---|---|
| Thickness | WSP 120.6 | mm | 0.18 |
| MD tensile strength | WSP 110.4 | N/50 mm | 20.11 |
| MD elongation | WSP 110.4 | % | 16.05 |
| CD tensile strength | WSP 110.4 | N/50 mm | 3.21 |

The second layer is a closed cell foamed polyethylene with thickness of 1 mm. In this case a known material like Cell-Aire was used. Said material has an elongation at break of 8.5 mm, a punching test resistance of 5.5 N according to standard SAC-PL 012 with a longitudinal tensile strength of 10.9 N and transverse tensile strength of 4 N according to standard DIN 53571 and a longitudinal elongation at break of 19.9% and transverse elongation at break of 34% according to standard DIN53571.

The initial thickness of the layer of non-woven fabric and of the closed cell foamed material is 0.28 mm and 1.25 respectively, the final thickness of the multilayer is 1.27 mm.

EXAMPLE V

With reference to example IV, the layer of non-woven fabric can be replaced by a polyethylene microperforated film formed of a microperforated material with 52 mesh in which the microperforations have been obtained with the known vacuum method, for example having the characteristics given in table 2:

TABLE 2

| Characteristics | Test method | Unit of measurement | Batch mean |
|---|---|---|---|
| Base weight | WSP 130.1 | g/m$^2$ | 10.35 |
| Thickness | WSP 120.6 | Mm | 0.30 |
| MD tensile strength | ASTM D882 | N/inch | 5.04 |

TABLE 2-continued

| Characteristics | Test method | Unit of measurement | Batch mean |
|---|---|---|---|
| MD elongation | ASTM D882 | % | 145.74 |
| CD tensile strength | ASTM D882 | N/inch | 2.13 |
| CD elongation | ASTM D882 | % | 415.07 |

It is therefore possible to process both web materials and films, i.e. continuous web materials.

The initial thickness of the layer of non-woven fabric and of the closed cell foamed material is 0.32 mm and 1.25 respectively, the final thickness of the multilayer is 1.53 mm.

Lastly it is clear that modifications or variations can be made to the method described and illustrated here without departing from the protective scope as defined by the attached claims.

By overall weight per square meter we mean the theoretical sum of the weight per square meter measured in $g/m^2$ of each single layer fed into the rollers 3, 4.

By feed-in thickness is intended, when the material is multilayer and there are no free fibres, the theoretical sum of the single layers.

The invention claimed is:

1. A method for producing a material comprising a perforated low density web of polyolefin material and having a final thickness of at least 0.20 mm, comprising the steps of:
   providing a layer of low density polyolefin web material that has a maximum total weight per square meter of 75 $g/m^2$ or lower; and
   processing the layer of low density polyolefin web material between two rollers pressing onto each other to obtain the perforated low density web of polyolefin material, wherein a first roller has protrusions to perforate the layer of low density polyolefin web material, and a second roller rotates at a different speed from that of the first roller and has projecting parts with contact areas arranged to perforate the layer of low density polyolefin web material with the protrusions, the contact areas being spaced by recesses to receive the layer of low density polyolefin web material and having larger dimensions than contact faces of the protrusions, the recesses leaving an impression in relief (I) on the layer of low density polyolefin web material and in that a thickness of the layer of low density polyolefin web material fed into the rollers is equal to or greater than a thickness of the perforated low density web of polyolefin material that is output from the rollers and in that the recesses have a first maximum height (h2) and the protrusion have a second maximum height (h1) and in that the thickness of the perforated low density web of polyolefin material fed out from the first and second rollers is greater than or equal to at least one of the first or second maximum height (h1, h2).

2. The method according to claim 1, wherein an area of the recesses is at least equal to or greater than an area of the contact areas.

3. The method according to claim 1, wherein the contact areas are elongated and have a maximum longitudinal dimension at least four times greater than a maximum transverse dimension.

4. The method according to claim 1, wherein said layer of low density polyolefin web material is hydrophobic.

5. The method according to claim 1, wherein the layer of low density polyolefin web material comprises a closed cell foamed layer.

6. The method according to claim 1, wherein the step of providing the layer of low density polyolefin web material comprises the step of depositing free fibres on the layer of low density polyolefin web material.

7. The method according to claim 6, wherein the step of providing the layer of low density polyolefin web material comprises the step of covering the free fibres with a further layer of low density polyolefin web material to form a sandwich of low density polyolefin web materials.

8. The method according to claim 7, wherein the free fibres are made of a hydrophilic material.

9. The method according to claim 1, wherein the contact areas and/or the contact faces are offset from one another or have a longitudinal median plane (M) inclined with respect to a machine direction (MD) to reduce the wear on the rollers.

10. The method according to claim 9, wherein the contact areas follow a non-rectilinear profile.

11. The method according to claim 1, wherein the final thickness is at least 0.4 mm.

12. The method according to claim 9, wherein the contact areas follow a sinusoidal profile.

13. A method for producing a material comprising a perforated low density web of polyolefin material and having a final thickness of at least 0.20 mm, comprising the steps of:
   providing a layer of low density polyolefin web material that has a maximum total weight per square meter of 75 $g/m^2$ or lower; and
   processing the layer of low density polyolefin web material between two rollers pressing onto each other to obtain the perforated low density web of polyolefin material, wherein a first roller has protrusions to perforate the layer of low density polyolefin web material, and a second roller rotates at a different speed from that of the first roller and has projecting parts with first contact faces arranged, in combination with second contact faces of the protrusions to perforate the layer of low density polyolefin web material, the first contact faces being spaced by recesses to receive the layer of low density polyolefin web material and having larger dimensions than the second contact faces of the protrusions, wherein the first and second contact faces are co-planar, the recesses leaving an impression in relief (I) on the layer of low density polyolefin web material and in that a thickness of the layer of low density polyolefin web material fed into the rollers is equal to or greater than a thickness of the perforated low density web of polyolefin material that is output from the rollers and in that the recesses have a first maximum height (h2) and the protrusion have a second maximum height (h1) and in that the thickness of the perforated low density web of polyolefin material fed out from the first and second rollers is greater than or equal to at least one of the first or second maximum height (h1, h2).

* * * * *